(12) United States Patent
Nieendick et al.

(10) Patent No.: US 7,268,107 B2
(45) Date of Patent: Sep. 11, 2007

(54) HIGHLY CONCENTRATED, FREE-FLOWING PEARLY LUSTRE CONCENTRATES

(75) Inventors: Claus Nieendick, Krefeld (DE); Heike Kublik, Kempen (DE); Josef Koester, Duesseldorf (DE); Michael Lieu, Taipai (TW)

(73) Assignee: Cognis Deutschland GmbH & Co. KG, Duesseldorf (DE)

(*) Notice: Subject to any disclaimer, the term of this patent is extended or adjusted under 35 U.S.C. 154(b) by 192 days.

(21) Appl. No.: 10/499,186

(22) PCT Filed: Nov. 9, 2002

(86) PCT No.: PCT/EP02/13926

§ 371 (c)(1),
(2), (4) Date: Apr. 18, 2005

(87) PCT Pub. No.: WO03/052036

PCT Pub. Date: Jun. 26, 2003

(65) Prior Publication Data

US 2006/0079414 A1    Apr. 13, 2006

(30) Foreign Application Priority Data

Dec. 18, 2001 (DE) .............................. 101 62 026

(51) Int. Cl.
C11D 1/66 (2006.01)
C11D 1/825 (2006.01)
C11D 9/22 (2006.01)
A61K 8/30 (2006.01)
A61K 8/92 (2006.01)

(52) U.S. Cl. .................. 510/416; 510/119; 510/123; 510/126; 510/155; 424/401; 424/70.1; 424/70.19

(58) Field of Classification Search ............. 510/119, 510/123, 126, 155, 416; 424/401, 70.1, 70.19
See application file for complete search history.

(56) References Cited

U.S. PATENT DOCUMENTS

| | | | |
|---|---|---|---|
| 4,172,887 A | 10/1979 | Vanlerberghe et al. | |
| 4,777,038 A | 10/1988 | Scheuffgen | |
| 5,403,508 A | 4/1995 | Reng et al. | |
| 5,705,169 A | 1/1998 | Stein et al. | |
| 5,711,899 A | 1/1998 | Kawa et al. | |
| 5,730,960 A | 3/1998 | Stein et al. | |
| 5,945,091 A | 8/1999 | Habeck et al. | |
| 6,193,960 B1 | 2/2001 | Metzger et al. | |
| 6,727,217 B1* | 4/2004 | Nieendick et al. ......... | 510/416 |
| 6,835,700 B1* | 12/2004 | Nieendick et al. ......... | 510/119 |
| 7,056,379 B2* | 6/2006 | Nieendick et al. ......... | 106/502 |

FOREIGN PATENT DOCUMENTS

| | | |
|---|---|---|
| DE | 1165574 | 8/1960 |
| DE | 20 24 051 | 12/1971 |
| DE | 38 43 572 | 6/1990 |
| DE | 41 03 551 | 8/1992 |
| DE | 197 12 033 | 9/1998 |
| DE | 199 21 186 | 11/2000 |
| EP | 0 205 922 | 12/1986 |
| EP | 0 376 083 | 7/1990 |
| EP | 0 568 848 | 11/1993 |
| EP | 0 569 843 | 11/1993 |
| EP | 0 684 302 | 11/1995 |
| EP | 0 693 471 | 1/1996 |
| EP | 0 694 521 | 1/1996 |
| EP | 0 818 450 | 1/1998 |
| FR | 2 252 840 | 6/1975 |
| GB | 962919 | 7/1964 |
| GB | 1 333 475 | 10/1973 |
| WO | WO 00/68350 | * 11/2000 |
| WO | WO 00 68350 | 11/2000 |

OTHER PUBLICATIONS

Ansmann et al., "Perlglanz in modernen, tensidhaltigen Formulierungen", Parfuemerie und Kosmetik, 75, 1994, pp. 578-580.
Todd et al., "Volatile silicone fluids for cosmetic formulations", Cosmetics and Toiletries, vol. 91, (1976), pp. 29-32.
Lochhead et al., "Encyclopedia of Polymers and Thickeners for Cosmetics)", Cosmetics and Toiletries, vol. 108, 1993, pp. 95-135.
P. Finkel, "Formulierung kosmetischer Sonnenschutzmittel", SOFW Journal, 122, 1996, pp. 543-546, 548.
Kosmetikverordnung, Appendix 6, Parts A and B (no date).
"Kosmetische Färbemittel", Farbstoffkommission der Deutschen Forschungsgemeinschaft, Verlag Chemie, Weinheim, (1984), pp. 81-106.

* cited by examiner

Primary Examiner—Brian Mruk
(74) Attorney, Agent, or Firm—John F. Daniels; Daniel S. Ortiz

(57) ABSTRACT

A pearlizing composition containing: (a) from about 30 to 55% by weight of a pearlizing wax; (b) a nonionic emulsifier; (c) optionally, a zwitterionic emulsifier; (d) from about 0.1 to 5% by weight of a polyol ester; and (e) water, all weights being based on the weight of the composition, and wherein the sum of (a)+(b)+(c) is at least about 55% by weight, based on the weight of the composition, and wherein the sum of (b)+(c) is less than about 25% by weight, based on the weight of the composition, and wherein (b) and (d) are present in the composition in a ratio by weight of from about 5:1 to 10:1.

19 Claims, No Drawings

HIGHLY CONCENTRATED, FREE-FLOWING PEARLY LUSTRE CONCENTRATES

This application is a 371 of PCT/EP02/13926 filed Dec. 9, 2002.

BACKGROUND OF THE INVENTION

This invention relates to highly concentrated pearlizing concentrates with a high content of pearlizing waxes and a low content of emulsifiers and special emulsifier/polyol ester mixtures and to a process for their production.

Pearlizers are a long-established and proven medium for providing cosmetic products with an attractive, rich and interesting appearance. An overview of modern pearlizing formulations was published by A. Ansmann and R. Kawa in Parf. Kosm. 75, 578 (1994). The complex requirement profile these formulations have to satisfy includes such properties as high brilliance, good particle fineness and high compatibility with other auxiliaries, and performance requirements relating to processability. Particularly highly concentrated formulations intended for subsequent processing are expected to combine uniform, good physicochemical stability with low viscosity and flowability. Polyol fatty acid esters are often used as viscosity adjusters in the production of pearlizing concentrates.

There are various known formulations which provide surface-active compositions with the required pearlescence and in which polyol fatty acid esters are used. For example, German patent applications DE 3843572 A1 and DE 4103551 A1 (Henkel) describe pearlizing concentrates in the form of flowable aqueous dispersions which contain 15 to 40% by weight pearlizing components, 5 to 55% by weight emulsifiers and 0.1 to 5 or 15 to 40% by weight polyols. Polyol fatty acid esters, for example, were used in large quantities. They were also used in European patent application EP 0205922 A2 (Henkel). This application relates to flowable pearlizing concentrates containing 5 to 15% by weight acylated polyglycols, 1 to 6% by weight fatty acid monoethanolamides and 1 to 5% by weight nonionic emulsifiers. According to the teaching of European patent EP 0569843 B1 (Hoechst), nonionic flowable pearlizing dispersions may also be obtained by preparing mixtures of 5 to 30% by weight acylated polyglycols and 0.1 to 20% by weight selected nonionic surfactants. Finally, European patent application EP 0684302 A1 (Th. Goldschmidt) proposes the use of polyglycerol esters as crystallization aids for the production of pearlizing concentrates.

Although the pearlizing concentrates mentioned are of relatively high concentration, it has been found that the content of active substances can be further increased, even for low-viscosity flowable formulations.

As crucially relevant prior art, German patent application DE 199211186 A1 (Cognis) discloses highly concentrated flowable pearlizing concentrates with concentrations of at least 55% by weight which contain 25 to 45% by weight selected pearlizing waxes, 25 to 40% by weight nonionic emulsifiers and 0.5 to 15% by weight polyol esters. In these formulations, however, a high percentage content of emulsifiers is required to stabilize the pearlizing waxes. The ratio of pearlizing waxes to stabilizing emulsifiers is also equivalent and, where the concentrates are incorporated in formulations, can lead to incompatibilities with other auxiliaries.

Accordingly, the problem addressed by the present invention was to provide new pearlizing concentrates with a very high content of active substances which would be distinguished by a relatively small content of emulsifiers and by improved processability coupled with high stability and comparable performance in regard to the brilliance of the pearlescence.

DESCRIPTION OF THE INVENTION

The present invention relates to highly concentrated, flowable pearlizing concentrates containing (a) 30 to 55% by weight pearlizing waxes,
(b) less than 25% by weight emulsifiers from the group of nonionic emulsifiers and optionally from the group of zwitterionic emulsifiers and
(c) 0.1 to 5% by weight polyol esters, with the provisos that the quantities shown add up to 100% by weight with water and optionally other auxiliaries and additives, the sum of components (a), (b) and (c) is at least 55% by weight and the quantity ratio of nonionic emulsifiers to polyol esters is in the range from 5:1 to 10:1.

It has surprisingly been found that the content of emulsifiers can be reduced to below 25% by weight by using mixtures of nonionic emulsifiers and polyol esters in a ratio of 5:1 to 10:1. For the same physicochemical stability and a uniformly high concentration of active substances (corresponding to the sum of pearlizing waxes, emulsifiers/co-emulsifiers and polyol esters), viscosity can be further reduced and, hence, processability significantly improved, even for relatively small quantities.

This effect is particularly pronounced where the preferred nonionic emulsifiers, fatty alcohol ethoxylates, are used; without the addition of the polyol esters, they would contribute to a high viscosity. In addition, an increase in physicochemical stability is obtained when the nonionic emulsifiers are used in combination with zwitterionic emulsifiers.

The new pearlizing concentrates are also very finely particulate and provide water-based surfactant preparations with a particularly dense and brilliant pearlescence.

Pearlizing Waxes

Suitable pearlizing waxes are, for example, alkylene glycol esters, fatty acid alkanolamides, partial glycerides, esters of polybasic, optionally hydroxysubstituted carboxylic acids, fatty alcohols, fatty acids, fatty ketones, fatty aldehydes, fatty ethers, fatty carbonates, ring opening products of olefin epoxides and mixtures thereof.

The alkylene glycol esters which form component (a1) are normally monoesters and/or diesters of alkylene glycols corresponding to formula (I):

$$R^1CO(OA)_nOR^2 \qquad (I)$$

in which $R^1CO$ is a linear or branched, saturated or unsaturated acyl group containing 6 to 22 carbon atoms, $R^2$ is hydrogen or has the same meaning as $R^1CO$ and A is a linear or branched alkylene group containing 2 to 4 carbon atoms and n is a number of 1 to 5. Typical examples are monoesters and/or diesters of ethylene glycol, propylene glycol, diethylene glycol, dipropylene glycol, triethylene glycol or tetraethylene glycol with fatty acids containing 6 to 22 and preferably 12 to 18 carbon atoms, such as caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof.

Other pearlizing waxes, such as fatty acid alkanolamides, correspond to formula (II):

$$R^3CO—NR^4—B—OH \quad (II)$$

in which $R^3CO$ is a linear or branched, saturated or unsaturated acyl group containing 6 to 22 carbon atoms, $R^4$ is hydrogen or an optionally hydroxy-substituted alkyl group containing 1 to 4 carbon atoms and B is a linear or branched alkylene group containing 1 to 4 carbon atoms. Typical examples are condensation products of ethanolamine, methyl ethanol-amine, diethanolamine, propanolamine, methyl propanolamine and dipropanolamine and mixtures thereof with caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. Stearic acid ethanolamide is particularly preferred.

Partial glycerides are monoesters and/or diesters of glycerol with linear, saturated fatty acids, i.e. for example caproic acid, caprylic acid, capric acid, lauric acid, myristic acid, palmitic acid, palmitoleic acid, stearic acid, behenic acid and technical mixtures thereof. They correspond to formula (III):

$$\begin{array}{l} CH_2O(CH_2CH_2O)_x—COR^5 \\ CH—O(CH_2CH_2O)_yR^6 \\ CH_2O(CH_2CH_2O)_z—R^7 \end{array} \quad (III)$$

in which $R^5CO$ is a linear, saturated acyl group containing 6 to 22 carbon atoms, $R^6$ and $R^7$ independently of one another represent hydrogen or have the same meaning as $R^5CO$, x, y and z together stand for 0 or for a number of 1 to 30 and X is an alkali or alkaline earth metal, with the proviso that at least one of the two substituents $R^6$ and $R^7$ is hydrogen. Typical examples are lauric acid monoglyceride, lauric acid diglyceride, coconut fatty acid monoglyceride, coconut fatty acid triglyceride, palmitic acid monoglyceride, palmitic acid triglyceride, stearic acid monoglyceride, stearic acid diglyceride, tallow fatty acid monoglyceride, tallow fatty acid di-glyceride, behenic acid monoglyceride, behenic acid diglyceride and technical mixtures thereof which may still contain small quantities of triglyceride from the production process.

Another preferred group of pearlizing waxes are esters of polybasic, optionally hydroxysubstituted carboxylic acids with fatty alcohols containing 6 to 22 carbon atoms. The acid component of these esters may be selected, for example, from malonic acid, maleic acid, fumaric acid, adipic acid, sebacic acid, azelaic acid, dodecanedioic acid, phthalic acid, isophthalic acid and, more particularly, succinic acid and also malic acid, citric acid and, more particularly, tartaric acid and mixtures thereof. The fatty alcohols contain 6 to 22, preferably 12 to 18 and more preferably 16 to 18 carbon atoms in the alkyl chain. Typical examples are caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and technical mixtures thereof. The esters may be present as full or partial esters; monoesters and, above all, diesters of carboxylic or hydroxycarboxylic acids preferably being used. Typical examples are succinic acid mono- and dilauryl ester, succinic acid mono- and dicetearyl ester, succinic acid mono- and distearyl ester, tartaric acid mono- and dilauryl ester, tartaric acid mono- and dicocoalkyl ester, tartaric acid mono- and dicetearyl ester, citric acid mono-, di- and trilauryl ester, citric acid mono-, di- and tricocoalkyl ester and citric acid mono-, di- and tricetearyl ester.

A third group of pearlizing waxes are fatty alcohols and fatty acids corresponding to formulae (IVa and b):

$$R^8OH \quad (IVa)$$

$$R^8COOH \quad (IVb)$$

in which $R^8$ is a linear, optionally hydroxy-substituted alkyl group and/or acyl group containing 16 to 48 and preferably 18 to 36 carbon atoms. Typical examples of suitable alcohols are cetearyl alcohol, hydroxystearyl alcohol, behenyl alcohol and oxidation products of long-chain paraffins.

Fatty ketones preferably correspond to formula (V):

$$R^9—CO—R^{10} \quad (V)$$

in which $R^9$ and $R^{10}$ independently of one another represent alkyl and/or alkenyl groups containing 1 to 22 carbon atoms, with the proviso that they contain a total of at least 24 and preferably 32 to 48 carbon atoms. The ketones may be prepared by known methods, for example by pyrolysis of the corresponding fatty acid magnesium salts. The ketones may be symmetrical or non-symmetrical, although the two substituents $R^9$ and $R^{10}$ preferably differ from one another by only one carbon atom and are derived from fatty acids containing 16 to 22 carbon atoms.

Fatty aldehydes suitable as pearlizing waxes preferably correspond to formula (VI):

$$R^{11}COH \quad (VI)$$

in which $R^{11}CO$ is a linear or branched acyl group containing 24 to 48 and preferably 28 to 32 carbon atoms.

Other suitable pearlizing waxes are fatty ethers corresponding to formula (VII):

$$R^{12}—O—R^{13} \quad (VII)$$

in which $R^{12}$ and $R^{13}$ independently of one another represent alkyl and/or alkenyl groups containing 1 to 22 carbon atoms, with the proviso that they contain a total of at least 24 and preferably 32 to 48 carbon atoms. Fatty ethers of the type mentioned are normally prepared by acidic condensation of the corresponding fatty alcohols. Fatty ethers with particularly advantageous pearlizing properties are obtained by condensation of fatty alcohols containing 16 to 22 carbon atoms such as, for example, cetyl alcohol, cetearyl alcohol, stearyl alcohol, isostearyl alcohol, oleyl alcohol, behenyl alcohol and/or erucyl alcohol.

Other suitable pearlizing waxes are fatty carbonates corresponding to formula (VIII):

$$R^{14}O—CO—OR^{15} \quad (VIII)$$

in which $R^{14}$ and $R^{15}$ independently of one another are alkyl and/or alkenyl groups containing 1 to 22 carbon atoms, with the proviso that they contain a total of at least 24 and preferably 32 to 48 carbon atoms. The substances are obtained by transesterifying dimethyl or diethyl carbonate, for example, with the corresponding fatty alcohols by methods known per se. Accordingly, the fatty carbonates may be symmetrical or non-symmetrical. However, carbonates in which $R^{14}$ and $R^{15}$ are the same and represent alkyl groups containing 16 to 22 carbon atoms are preferably used. Transesterification products of dimethyl or diethyl carbonate with cetyl alcohol, cetearyl alcohol, stearyl alcohol, isostearyl alcohol, oleyl alcohol, behenyl alcohol and/or erucyl alcohol in the form of their monoesters and diesters and technical mixtures thereof are particularly preferred.

The ring-opening products are known substances which are normally obtained by acid-catalyzed reaction of terminal or internal olefin epoxides with aliphatic alcohols. The reaction products preferably correspond to formula (IX):

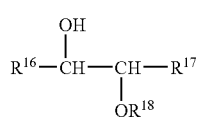

(IX)

in which $R^{16}$ and $R^{17}$ represent hydrogen or an alkyl group containing 10 to 20 carbon atoms, with the proviso that the sum total of carbon atoms of $R^{16}$ and $R^{17}$ is between 10 and 20 and $R^{18}$ is an alkyl and/or alkenyl group containing 12 to 22 and/or the residue of a polyol containing 2 to 15 carbon atoms and 2 to 10 hydroxyl groups. Typical examples are ring-opening products of α-dodecene epoxide, α-hexadecene epoxide, α-octadecene epoxide, α-eicosene epoxide, α-docosene epoxide, i-dodecene epoxide, i-hexadecene epoxide, i-octadecene epoxide, i-eicosene epoxide and/or i-docosene epoxide with lauryl alcohol, cocofatty alcohol, myristyl alcohol, cetyl alcohol, cetearyl alcohol, stearyl alcohol, isostearyl alcohol, oleyl alcohol, elaidyl alcohol, petroselinyl alcohol, linolyl alcohol, linolenyl alcohol, behenyl alcohol and/or erucyl alcohol. Ring opening products of hexa- and/or octadecene epoxides with fatty alcohols containing 16 to 18 carbon atoms are preferably used. If polyols are used instead of the fatty alcohols for the ring opening reaction, they are selected for example from the following substances: glycerol; alkylene glycols such as, for example, ethylene glycol, diethylene glycol, propylene glycol, butylene glycol, hexylene glycol and polyethylene glycols with an average molecular weight of 100 to 1,000 dalton; technical oligoglycerol mixtures with a degree of self-condensation of 1.5 to 10 such as, for example, technical diglycerol mixtures with a diglycerol content of 40 to 50% by weight; methylol compounds such as, in particular, trimethylol ethane, trimethylol propane, trimethylol butane, pentaerythritol and dipentaerythritol; lower alkyl glucosides, more particularly those containing 1 to 8 carbon atoms in the alkyl chain such as, for example, methyl and butyl glucoside; sugar alcohols containing 5 to 12 carbon atoms such as, for example, sorbitol or mannitol, sugars containing 5 to 12 carbon atoms such as, for example, glucose or sucrose; amino sugars such as, for example, glucamine.

Preferred pearlizing waxes are alkylene glycol fatty acid esters corresponding to formula (I) in quantities of 30 to 50% by weight, preferably in quantities of 36 to 45% by weight and more particularly in quantities of 37 to 41% by weight, based on the bearlizing concentrates. Among these pearlizing waxes, ethylene glycol mono- and/or distearate is/are particularly preferred for sparkling pearlescence. The best results are obtained with ethylene glycol distearate.

Nonionic Emulsifiers

Suitable nonionic emulsifiers (component b) are, for example, nonionic surfactants from at least one of the following groups:

(b1) products of the addition of 2 to 30 mol ethylene oxide and/or 0 to 5 mol propylene oxide onto linear $C_{8-22}$ fatty alcohols, onto $C_{12-22}$ fatty acids, onto alkyl phenols containing 8 to 15 carbon atoms in the alkyl group and onto alkyl amines containing 8 to 22 carbon atoms in the alkyl group;

(b2) alkyl mono- and oligoglycosides containing 8 to 22 carbon atoms in the alkyl group and ethoxylated analogs thereof;

(b3) products of the additon of 1 to 15 mol ethylene oxide onto castor oil and/or hydrogenated castor oil;

(b4) products of the addition of 15 to 60 mol ethylene oxide onto castor oil and/or hydrogenated castor oil;

(b5) mono-, di- and trialkyl phosphates and mono-, di- and/or tri-PEG-alkyl phosphates and salts thereof;

(b6) wool wax alcohols;

(b7) polysiloxane/polyalkyl polyether copolymers and corresponding derivatives;

(b8) polyalkylene glycols and (b9) glycerol carbonate.

The addition products of ethylene oxide and/or propylene oxide onto fatty alcohols, fatty acids, alkylphenols or onto castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers from DE 2024051 PS. $C_{8/18}$ alkyl mono- and oligoglycosides, their production and their use are known from the prior art. They are produced in particular by reacting glucose or oligosaccharides with primary $C_{8-18}$ alcohols. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Fatty alcohol ethoxylates and especially fatty alcohol ethoxylates of $C_{12/14}$ fatty alcohols containing 2 to 6 ethylene oxide units are particularly preferred for the purposes of the present invention.

Zwitterionic Emulsifiers

In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacyl aminoethyl hydroxyethyl carboxymethyl glycinate.

Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-coco-alkylaminopropionate, cocoacylaminoethyl aminopropionate and $C_{12/18}$ acyl sarcosine.

Particularly preferred zwitterionic or ampholytic surfactants are betaines and, of these, especially the fatty acid amide derivative known under the CTFA name of Cocoamidopropyl Betaine.

The total emulsifier content should be below 25% by weight, preferably below 20% by weight and more particularly between 10 and 18% by weight, based on the quantity of the pearlizing concentrates. The quantity ratio of pearlizing waxes to total emulsifier is then between 7:1 and 2:1, preferably between 3.5:1 and 2.3:1 and more preferably between 2.7:1 and 2.4:1.

With regard to the physicochemical stability of the concentrates, it has proved to be particularly suitable to use the nonionic emulsifiers in the form of mixtures with zwitterionic emulsifiers. The quantity ratio of nonionic to zwitterionic emulsifiers should then be between 0.5:1 and 5:1 and is preferably between 1:1 and 2:1 and, more particularly, substantially equivalent at 1:1 to 1.2:1.

The pearlizing concentrates should preferably be free from anionic surfactants.

Polyol Esters

Polyol esters which—as co-emulsifiers—form component (c) may be selected from the following groups of compounds:

(c1) partial esters of glycerol and/or sorbitan with unsaturated, linear or saturated, branched fatty acids containing 12 to 22 carbon atoms and/or hydroxycarboxylic acids containing 3 to 18 carbon atoms and adducts thereof with 1 to 30 mol ethylene oxide;

(c2) partial esters of polyglycerol (average degree of self-condensation 2 to 8), polyethylene glycol (molecular weight 400 to 5000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and adducts thereof with 1 to 30 mol ethylene oxide;

(c3) mixed esters of pentaerythritol, fatty acids, citric acid and fatty alcohol according to DE 1165574 PS and/or mixed esters of fatty acids containing 6 to 22 carbon atoms, methyl glucose and polyols, preferably glycerol or polyglycerol.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide with the partial glycerides mentioned are also suitable.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohyd roxystea rate, sorbitan sesquihydroxystearate, sorbitan dihydroxystearate, sorbitan trihydroxy-stearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof.

Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Preferred polyol esters for the purposes of the present invention are ethoxylated partial glycerides with 1 to 30 and preferably 5 to 10 mol ethylene oxide. They are used in quantities of 0.1 to 5% by weight, preferably in quantities of 0.3 to 3% by weight and more particularly in quantities of 0.5 to 1.5% by weight, based on the quantity of the pearlizing concentrates.

The quantity ratio of nonionic emulsifiers (nonionic surfactants) to polyol esters advantageous for viscosity adjustment is 5:1 to 10:1, preferably 6:1 to 9:1 and more particularly 7.5:1 to 8:1.

Polyols

In a preferred embodiment of the invention, the concentrates may additionally contain *polyols as an optional component (e) for reducing viscosity. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol;

sugars containing 5 to 12 carbon atoms, for example glucose or sucrose;

amino sugars, for example glucamine;

dialcoholamines, such as diethanolamine or 2-aminopropane-1,3-diol.

The polyols are used in quantities of typically 0.1 to 10% by weight, preferably 0.5 to 5% by weight and more particularly 0.7 to 1% by weight, based on the quantity of the pearlizing concentrates. If larger quantities of polyol, preferably glycerol or ethylene glycol, are used, the concentrates are simultaneously stabilized against microbial infestation.

Production Process

In one preferred embodiment, which is also a subject of the invention, the pearlizing concentrates are produced by preparing a mixture of components (a), (b) and (c), heating it to a temperature 1 to 30° C. above the melting point of the mixture, mixing it with the necessary quantity of water having substantially the same temperature and then cooling the mixture to room temperature. In an alternative method of production, a concentrated aqueous surfactant paste may be initially introduced, the pearlizing wax stirred in while heating and the mixture subsequently diluted with more water to the required concentration or the mixing step may be carried out in the presence of polymeric hydrophilic thickeners such as, for example, hydroxypropyl celluloses, xanthan gum or polymers of the Carbomer type.

Commercial Applications

The pearlizing concentrates according to the invention typically have the following composition:
(a) 30 to 55% by weight pearlizing waxes,
(b) less than 25% by weight emulsifiers from the group of nonionic emulsifiers and optionally from the group of zwitterionic emulsifiers and
(c) 0.1 to 5% by weight polyol esters, with the provisos that the quantities shown add up to 100% by weight with water and optionally other auxiliaries and additives, the sum of components (a), (b) and (c) is at least 55% by weight and the quantity ratio of nonionic emulsifiers to polyol esters is in the range from 5:1 to 10:1.

The pearlizing concentrates according to the invention preferably have the following composition:
(a) 36 to 45% by weight pearlizing waxes,
(b1) 3 to 12% by weight nonionic emulsifiers and
(b2) 3 to 12% by weight zwitterionic emulsifiers and
(c) 0.3 to 3% by weight polyol esters, with the provisos that the quantities shown add up to 100% by weight with water and optionally other auxiliaries and additives, the sum of components (a), (b) and (c) is at least 55% by weight, the quantity ratio of nonionic emulsifiers to polyol esters is in the range from 5:1 to 10:1 and the quantity ratio of pearlizing waxes to emulsifiers is in the range from 3.5:1 to 2.3:1.

The particularly preferred composition of the pearlizing concentrates according to the invention is:
(a) 37 to 41% by weight pearlizing waxes,
(b1) 4 to 10% by weight nonionic emulsifiers and
(b2) 4 to 10% by weight zwitterionic emulsifiers and
(c) 0.5 to 1.5% by weight polyol esters and
(d) 0 to 5% by weight polyols, with the provisos that the quantities shown add up to 100% by weight with water and optionally other auxiliaries and additives, the sum of components (a), (b) and (c) is at least 55% by weight, the quantity ratio of nonionic emulsifiers to polyol esters is in the range from 6:1 to 9:1 and the quantity ratio of pearlizing waxes to emulsifiers is in the range from 2.7:1 to 2.4:1.

The pearlizing concentrates according to the invention are suitable for opacifying surface-active preparations such as, for example, hair shampoos or manual dishwashing detergents. To produce opacified and pearlescent, liquid water-based preparations of water-soluble surfactants, the pearlizing concentrates are added to the clear water-based preparations in a quantity of 0.5 to 40% by weight, preferably 1 to 20% by weight and more particularly 2 to 10% by weight, normally at 0 to 40° C., and are distributed therein by stirring.

Cosmetic and/or Pharmaceutical Preparations

The pearlizing concentrates according to the invention may be used for the production of cosmetic and/or pharmaceutical preparations, for example hair shampoos, hair lotions, foam baths, shower baths, creams, gels, lotions, alcoholic and aqueous/alcoholic solutions, emulsions, wax/fat compounds, stick preparations, powders or ointments. These preparations may also contain mild surfactants, oil components, superfatting agents, consistency factors, thickeners, polymers, silicone compounds, fats, waxes, stabilizers, biogenic agents, deodorizers, antiperspirants, antidandruff agents, film formers, swelling agents, UV protection factors, antioxidants, hydrotropes, preservatives, insect repellents, self-tanning agents, solubilizers, perfume oils, dyes and the like as further auxiliaries and additives.

Typical examples of suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines and/or protein fatty acid condensates, preferably based on wheat proteins.

Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, emucyl isostearate, erucyl oleate, erucyl behenate and erucyl erucate. Also suitable are esters of linear $C_{6-22}$ fatty acids with branched alcohols, more particularly 2-ethyl hexanol, esters of hydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons, for example squalane, squalene or dialkyl cyclohexanes.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Suitable thickeners are, for example, Aerosil types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol mono-esters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylamino-hydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR 2252840 A and crosslinked water-soluble polymers thereof, cationic chitin derivatives such as, for example, quaternized chitosan, optionally in micro-crystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Mirapol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Typical examples of fats are glycerides while suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes, microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers.

Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chloro-phenoxy)-propane-1,2-diol, 3-iodo-2-propinyl butyl carbamate, chlorhexidine, 3,4,4'-trichlorocarbanilide (TTC), antibacterial perfumes, thymol, thyme oil, eugenol, nettle oil, menthol, mint oil, farnesol, phenoxyethanol, glycerol monolaurate (GML), diglycerol monocaprate (DMC), salicylic acid-N-alkylamides such as, for example, salicylic acid-n-octyl amide or salicylic acid-n-decyl amide.

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT, Henkel KGaA, Dusseldorf, FRG). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of labdanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic fragrances. Natural fragrances include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxy-citronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetate, cyclamen aldehyde, linalool, Bois-ambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Antiperspirants reduce perspiration and thus counteract underarm wetness and body odor by influencing the activity of the eccrine sweat glands. Aqueous or water-free antiperspirant formulations typically contain the following ingredients:
(a) astringent active principles,
(b) oil components,
(c) nonionic emulsifiers,
(d) co-emulsifiers,
(e) consistency factors,
(f) auxiliaries in the form of, for example, thickeners or complexing agents and/or
(g) nonaqueous solvents such as, for example, ethanol, propylene glycol and/or glycerol.

Suitable astringent active principles of antiperspirants are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Oil-soluble and water-soluble auxiliaries typically encountered in antiperspirants may also be present in relatively small amounts. Oil-soluble auxiliaries such as these include, for example,
inflammation-inhibiting, skin-protecting or pleasant-smelling essential oils,
synthetic skin-protecting agents and/or
oil-soluble perfume oils.

Typical water-soluble additives are, for example, preservatives, water-soluble perfumes, pH regulators, for example buffer mixtures, water-soluble thickeners, for example water-soluble natural or synthetic polymers such as, for example, xanthan gum, hydroxyethyl cellulose, polyvinyl pyrrolidone or high molecular weight polyethylene oxides.

Suitable antidandruff agents are climbazol, octopirox and zinc pyrithione.

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable swelling agents for aqueous phases are montmorillonites, clay minerals, Pemulen and alkyl-modified Carbopol types (Goodrich). Other suitable polymers and swelling agents can be found in R. Lochhead's review in Cosm. Toil. 108, 95 (1993).

Examples of UV protection factors include organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:
3-benzylidene camphor or 3-benzylidene norcamphor and derivatives thereof, for example 3-(4-methylbenzylidene)-camphor, as described in EP 0693471 B1;
4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-ethylhexyl ester;

triazine derivatives such as, for example, 2,4,6-trianilino-(p-carbo-2'-ethyl-1'-hexyloxy)-1,3,5-triazine and Octyl Triazone, as described in EP 0818450 A1, or Dioctyl Butamido Triazine (Uvasorb® HEB);

propane-1,3-diones such as, for example, 1-(4-tert.butylphenyl)-3-(4'-methoxyphenyl)-propane-1,3-dione;

ketotricyclo(5.2.1)decane derivatives, as described in EP 0694521 B1.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example 1-(4'-tert.butylphenyl)-3-(4'-methoxyphenyl)-propane-1,3-dione, 4-tert-butyl-4'-methoxydibenzoylmethane (Parsol 1789), 1-phenyl-3-(4'-isopropylphenyl)-propane-1,3-dione and the eneamine compounds described in DE 19712033 A1 (BASF). The UV-A and UV-B filters may of course also be used in the form of mixtures. Besides the soluble substances mentioned, insoluble pigments, i.e. finely dispersed metal oxides or salts, may also be used for this purpose. Examples of suitable metal oxides are, in particular, zinc oxide and titanium dioxide and also oxides of iron, zirconium, silicon, manganese, aluminium and cerium and mixtures thereof. Silicates (talcum), barium sulfate and zinc stearate may be used as salts. The oxides and salts are used in the form of the pigments for skin-care and skin-protecting emulsions. The particles should have an average diameter of less than 100 nm, preferably from 5 to 50 nm and more preferably from 15 to 30 nm. They may be spherical in shape although ellipsoidal particles or other non-spherical particles may also be used. The pigments may also be surface-treated, i.e. hydrophilicized or hydrophobicized. Typical examples are coated titanium dioxides such as, for example, Titandioxid T 805 (Degussa) or Eusolex® T2000 (Merck). Suitable hydrophobic coating materials are, above all, silicones and particularly trialkoxyoctyl silanes or simethicones. So-called micro- or nanopigments are preferably used in sun protection products. Micronized zinc oxide is preferably used. Other suitable UV filters can be found in P. Finkel's review in SÖFW-Journal 122, 543 (1996).

Besides the two above-mentioned groups of primary protection factors, secondary protection factors of the antioxidant type may also be used. Secondary sun protection factors of the antioxidant type interrupt the photochemical reaction chain which is initiated when UV rays penetrate into the skin. Typical examples of suitable antioxidants are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmol to μmol/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxy-butyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

In addition, hydrotropes, for example ethanol, isopropyl alcohol or polyols, may be used to improve flow behavior.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Ethyl Butylacetyl-aminopropionate. A suitable self-tanning agent is dihydroxyacetone.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular composition. The compositions may be produced by standard hot or cold processes and are preferably produced by the phase inversion temperature method.

EXAMPLES

The viscosity of pearlizing concentrates 1 to 4 according to the invention and comparison mixtures C1 to C3, C5 and C6 was determined by the Brookfield method in an RVT viscosimeter (23° C., 10 r.p.m., spindle 5). In the case of the highly concentrated formulations of low emulsifier content (C1 to C3), it is clear that only the addition of polyol esters leads to a low . . . flowable preparation. Where low concentration formulations with a relatively high emulsifier content (C5 and C6) are used, the addition of polyol esters does not lead to a significant change in viscosity.

TABLE 1

Composition and performance of pearlizing concentrates [quantities in % by weight active substance]

| Composition | C1 | C2 | C3 | 1 | 2 | 3 | 4 | C5 | C6 |
|---|---|---|---|---|---|---|---|---|---|
| Ethyleneglycol Distearate Cutina ® AGS | 40.0 | 40.0 | 40.0 | 40.0 | 40.0 | 40.0 | 40.0 | 27.0 | 27.0 |
| C12/14 Fatty alcohol + 4 EO Dehydol ® LS4 | 9.0 | — | — | 8.0 | — | — | 10.0 | 10.0 | 9.0 |
| C12/14 Fatty alcohol + 6 EO Dehydol ® LS6 | — | 7.0 | — | — | 6.0 | — | — | — | — |
| PEG-7-Glycerol Cocoate Cetiol ® HE | — | — | — | 1.0 | 1.0 | 1.4 | — | — | 1.0 |
| PEG-5-Cocoate | — | — | — | — | — | — | 1.0 | — | — |
| Coco Glucosides Plantacare ® 818 | — | — | 9.0 | — | — | 8.0 | — | — | — |
| Cocamidopropyl Betaine Dehyton ® K | 8.0 | 10.0 | 4.0 | 8.0 | — | 4.0 | 7.0 | 7.0 | 7.0 |
| Benzoic acid | 0.5 | 0.5 | 0.5 | 0.5 | 0.5 | 0.5 | 0.5 | 0.5 | 0.5 |
| Water | | | | to 100 | | | | | |
| Viscosity of the concentrates [mPas] | >100,000 | >100,000 | >100000 | 9600 | 9800 | 8500 | 9900 | 6100 | 5900 |
| Ratio of nonionic surfactant to polyol ester | — | — | — | 8:1 | 6:1 | 5.7:1 | 10:1 | — | 9:1 |
| Ratio of pearlizing wax to emulsifiers | 2.4:1 | 2.4:1 | 3.1:1 | 2.5:1 | 6.7:1 | 3; 3:1 | 2.4:1 | 1.6:1 | 1.7:1 |

The invention claimed is:

1. A pearlizing composition comprising:
  (a) from about 30 to 55% by weight of a pearlizing wax;
  (b) a nonionic emulsifier;
  (c) optionally, a zwitterionic emulsifier;
  (d) from about 0.1 to 5% by weight of a polyol ester; and
  (e) water, all weights being based on the weight of the composition, and wherein the sum of (a)+(b)+(c) is at least about 55% by weight, based on the weight of the composition, and wherein the sum of (b)+(c) is less than 25% by weight, based on the weight of the composition, and wherein (b) and (d) are present in the composition in a ratio by weight of from about 5:1 to 10:1.

2. The composition of claim 1 wherein (b) is a fatty alcohol ethoxylate.

3. The composition of claim 1 wherein (a) is present in the composition in an amount of from about 37 to 41% by weight, based on the weight of the composition.

4. The composition of claim 1 wherein the sum of (b)+(c) is from about 10 to 18% by weight, based on the weight of the composition.

5. The composition of claim 1 wherein the composition is free of anionic surfactants.

6. The composition of claim 1 wherein (d) is present in the composition in an amount of from about 0.5 to 1.5% by weight, based on the weight of the composition.

7. The composition of claim 1 wherein (d) is an ethoxylated partial glyceride.

8. The composition of claim 1 wherein (a) is present in an amount of from about 36 to 45% by weight, (b) is present in an amount of from about 3 to 12% by weight, (c) is present in an amount of from about 3 to 12% by weight, (d) is present in an amount of from about 0.3 to 3% by weight, all weights being based on the weight of the composition.

9. A process for imparting pearlescence to a product comprising adding to a water based preparation comprising water soluble surfactants a pearlescent composition containing:
  (a) from about 30 to 55% by weight of a pearlizing wax;
  (b) a nonionic emulsifier;
  (c) optionally, a zwitterionic emulsifier;
  (d) from about 0.1 to 5% by weight of a polyol ester; and
  (e) water, all weights being based on the weight of the composition, and wherein the sum of (a)+(b)+(c) is at least about 55% by weight, based on the weight of the composition, and wherein the sum of (b)+(c) is less than 25% by weight, based on the weight of the composition, and wherein (b) and (d) are present in the composition in a ratio by weight of from about 5:1 to 10:1.

10. The process of claim 9 wherein (b) is a fatty alcohol ethoxylate.

11. The process of claim 9 wherein (a) is present in the composition in an amount of from about 37 to 41% by weight, based on the weight of the composition.

12. The process of claim 9 wherein the sum of (b)+(c) is from about 10 to 18% by weight, based on the weight of the composition.

13. The process of claim 9 wherein the composition is free of anionic surfactants.

14. The process of claim 9 wherein (d) is present in the composition in an amount of from about 0.5 to 1.5% by weight, based on the weight of the composition.

15. The process of claim 9 wherein (d) is an ethoxylated partial glyceride.

16. The process of claim 9 wherein the composition contains (a) in an amount of from about 36 to 45% by weight, (b) in an amount of from about 3 to 12% by weight, (c) in an amount of from about 3 to 12% by weight, and (d) in an amount of from about 0.3 to 3% by weight, all weights being based on the weight of the composition.

17. The process of claim 9, wherein, from 0.5% to 40% by weight of the pearlescent composition is added to the water based preparation, wherein, the percent by weight is based on the weight of the water based preparation.

18. The process of claim 9, wherein, from 1% to 20% by weight of the pearlescent composition is added to the water based preparation, wherein, the percent by weight is based on the weight of the water based preparation.

19. The process of claim 9, wherein, from 2% to 10% by weight of the pearlescent composition is added to the water based preparation, wherein, the percent by weight is based on the weight of the water based preparation.

* * * * *